US006100068A

United States Patent [19]
Paik

[11] Patent Number: 6,100,068
[45] Date of Patent: Aug. 8, 2000

[54] METHOD OF PROTEIN PRODUCTION USING MITOCHONDRIAL TRANSLATION SYSTEM

[75] Inventor: Kye-Hyung Paik, Ranch Santa Fe, Calif.

[73] Assignee: Paik-Inje Memorial Institute for Biomedical Science, La Jolla, Calif.

[21] Appl. No.: 09/124,638

[22] Filed: Jul. 29, 1998

Related U.S. Application Data

[63] Continuation of application No. PCT/US97/00601, Jan. 21, 1997
[60] Provisional application No. 60/010,717, Jan. 29, 1996.
[51] Int. Cl.[7] ................................... C12N 15/09
[52] U.S. Cl. ........................ 435/69.3; 435/69.1; 435/70.1; 435/70.3
[58] Field of Search .............................. 435/1.1, 41, 69.1, 435/69.3, 70.1, 70.3, 440, 455, 325, 352, 353, 354, 362, 363, 366, 369, 370; 530/300, 350; 424/184, 189.1, 186.1, 204.1, 225.1, 226.1, 227.1, 228.1, 93.21

[56] References Cited

PUBLICATIONS

Zuckerman et al. The American Journal of the Medical Sciences. vol. 270(1), pp. 197–204, 1975.
Cheng et al. Journal of Virology. vol. 61(4), pp. 1286–1290, Apr. 1987.
Belyaev et al. Doklady Akademi Nauk SSSR, vol. 314(2), pp. 488–491 (translation), Sep. 1990.
Alberts, Bruce, et al., *Molecular Biology of the Cell, Second Edition*, Garland Publishing, Inc., New York & London, Chapter 7, pp. 387–401, 1989.
Jensen, T.G., et al., *Biochimica et Biophysica Acta*, 1180: 65–72, 1992, "Expression of wild–typ and mutant medium–chain acyl–CoA dehydrogenase (MCAD) cDNA in eucaryotic cells."
Araki, Kimi, et al., *Proc. Natl., Acad. Sci. USA*, 86: 207–211, Jan. 1989, "Expression and replication of hepatitis B virus genome in transgenic mice."
Chang, Ghien–Neng, et al., *The Journal of Biological Chemistry*, 267(31): 22414–22420, Nov. 5, 1992, "Biochemical Pharmacology of (+)—and (–)—2', 3'—Dideoxy–3'-thiacytidine as Anti–hepatitis B Virus Agents."
Chisari, Francis V., *Hepatology*, 22(4): 1316–1325, 1995, "Hepatitis B Virus Transgenic Mice: Insights Into the Virus and the Disease."
Colacino, J.M., S.K. Malcolm, and S.R. Jaskunas, *Antimicrobial Agents and Chemotherapy*, 38(9): 1997–2002, Sep. 1994, "Effect of Fialuridine on Replication of Mitochondrial DNA in CEM Cells and in Human Hepatoblastoma Cells in Culture."
Doong, Shin–Lian, et al., *Proc. Natl. Acad. Sci. USA*, 88: 8495–8499, Oct. 1991, "Inhibition of the replication of hepatitis B virus in vitro by 2', 3'–dideoxy–3'–thiacytidine and related analogues."
Elfassi, Emile, et al., *Proc. Natl. Acad. Sci. USA*, 81: 3526–3528, Jun. 1984, "Evidence of extrchromosoma forms of hepatitis B viral DNA in a bone marrow culture obtained from a patient recently infected with hepatitis B virus."
Féray, C., et al., *Transplantation*, 49(6): 1155–1158, Jun. 1990, "Persistent Hepatitis B Virus Infection of Mononuclear Blood Cells without Concomitant Liver Infection."
Cuidotti, Luca G., Brent Matzke, Heinz Schaller, and Francis Chisari, *Journal of Virology*, 69(10): 6158–6169, Oct. 1995, "High–Level Hepatitis B Virus Replication in Transgenic Mice."
Gripon, Phillippe, Christian Diot, and Christiane Gugen–Guillouzo, *Virology*, 192: 534–540, 1993, "Reproducible High Level Infection of Cultured Adult Human Hepatocytes by Hepatitis B Virus: Effect of Polyethylene Gycol on Adsorption and Penetration."
Kato, Nobuyuki, et al., *Proc. Natl. Acad. Sci. USA*, 87: 9524–9528, Dec. 1990, "Molecular cloning of the human hepatitis C virus genome from Japanese patients with non–A, non–B hepatitis."
Lau, Johnson, Y.N. and Teresa L. Wright, *The Lancet*, 342:1335–1340, Nov. 17, 1993, "Molecular virology and pathogenesis of hepatitis B."
Ochiya, Takahiro, et al., *Proc. Natl. Acad. Sci. USA*, 86: 1875–1879, Mar. 1989, "An in vitro system for infection with hepatitis B virus that uses primary human fetal hepatocytes."
Okaomoto, Hiroaki and Shunji Mishiro, *Intervirology*, 37: 68–76, 1994, "Genetic Heterogeneity of Hepatitis C Virus."
Paik, K–H, et al., *Hepatology*, 22(4), Pt. 2, AASLD Abstracts, Abstract 1459, 1995, "The Mitochondron is the Key Organelle for Hepatitis B Virus Infection."
Peränen, Johan, *Journal of General Virology*, 72: 195–199, 1991, "Localization and phosphorylation of Semliki Forest virus non–structureal protein nsP3 expressed in COS cells from a cloned cDNA."
Shavrina Asher, Ludmila V, Leonard N. Binn, and Ruth H. Marchwicki, *Journal of Virology Methods*, 15: 323–328, 1987. "Demonstration of hepatitis A virus in a cell culture by electron microscopy with immunoperoxidase staining."
Shimizu, Yohko, et al., *Proc. Natl. Acad. Sci. USA*, 89: 5477–5481, Jun. 1992, "Evidence for in vitro replicationof hepatitis C virus genome in a human T–cell line."
Smith, P.F., et al., *Life Sciences*, 36: 1367–1375, Nov. 14, 1985, "Dynamic Organ Culture of Precision Liver Slices for In Vitro Toxicology."
Yang, Young–II, and Kye–Hyung Paik, Manuscript, not yet submitted for publication, "Replication of Human Hepatitis B Virus (HBV) Genome in Rats Evidenced by Covalently Closed Circular DNA (CCC DNA)."

*Primary Examiner*—Remy Yucel
*Attorney, Agent, or Firm*—Knobbe, Martens, Olson & Bear, LLP

[57] ABSTRACT

A method of producing viral antigens in vitro by infecting animal organ tissue rich in mitochondria with a virus, including human hepatitis B virus (HBV), and culturing the infected tissue in vitro is disclosed. A method of producing proteins in vitro by transfecting mitochondria-rich animal tissue with a recombinant HBV-based vector and culturing the transfected tissue in a dynamic tissue culture system is disclosed.

11 Claims, 2 Drawing Sheets

METHOD OF PROTEIN PRODUCTION USING MITOCHONDRIAL TRANSLATION SYSTEM

RELATED APPLICATIONS

This application is a continuation of prior International Application PCT/US97/00601 filed on Jan. 21, 1997, which claims priority under 35 U.S.C. § 119(e) Provisional Application 60/010,717, filed on Jan. 29, 1996.

FIELD OF THE INVENTION

The present invention relates to protein expression of recombinant nucleic acid molecules, and specifically relates to producing proteins, including viral proteins, in animal tissue cultured in vitro by infecting the host tissue with a virus or transfecting the host tissue with a recombinant nucleic acid in a virus-based expression vector and utilizing translation in mitochondria-rich tissue.

DESCRIPTION OF THE PRIOR ART

Translation of proteins from transfected nucleic acids generally is accomplished using the universal translation systems present in prokaryotic or eucaryotic cells (Sambrook et al., *Molecular Cloning. A Laboratory Manual*, 2nd Ed., Vol. 1–3, Cold Spring Harbor Laboratory, Cold Spring Harbor, N.Y., 1989). Mitochondria found in eucaryotic cells have transcription and translation systems for expression of the endogenous mitochondrial DNA (mtDNA) that use a non-universal genetic code. The mitochondrial translation system, however, has not been used to translate foreign nucleic acids.

Mitochondria are multilayer membranous cellular organelles that grow and divide in a coordinated process that requires contributions from the genetic system in the nucleus of the cell and the separate genetic system contained in the mitochondria (Alberts et al., *Molecular Biology of The Cell*, 2nd Ed., pp. 387–401, Garland Publishing, Inc., New York, N.Y.). Most mitochondrial proteins are encoded by nuclear DNA that is transcribed, translated in the cytosol and imported into the mitochondria. In contrast, some mitochondrial proteins are transcribed from mtDNA and translated within the organelle itself using the mitochondrial system that includes two ribosomal RNA and 22 tRNAs. Comparison of the mitochondrial gene sequences with the amino acid sequences of the encoded proteins revealed that the genetic code within mitochondria is altered compared to the universal code used in the nucleus of eucaryotic cells and in most prokaryotes. For example, the UGA codon is a stop codon for protein synthesis in the universal code whereas UGA codes for tryptophan in mitochondria, and the codons AGA and AGG code for arginine in the universal system but are stop codons in mammalian mitochondria.

Recombinant DNA can be used to produce proteins that are transported into mitochondria. In one expression system, monkey kidney cells (COS-7 cells) were transfected with an expression vector containing a cDNA for a initochondrial flavoenzyme (MCAD) gene (Jensen et al., *Biochim. et Biophys. Acta* 1180: 65–72, 1992). RNA transcripts and protein were produced using the transfected cells' transcription and translation systems. The recombinant MCAD protein was processed and concentrated in a mitochondrial cell fraction indicating that the MCAD protein was transported into the mitochondria where a leader peptide was removed from the cytosol-produced protein.

Replication of certain viruses has been associated with cellular mitochondria or multilayer membranous vesicles found in infected cells. In monkey kidney cells grown in vitro and infected with hepatitis A virus (HAV), virus-Eke particles were found in membrane-bound vesicular inclusion bodies that contain HAV antigens (Asher et al., *J.Virol. Meth.* 15:323–328, 1987). A phosphoprotein required for RNA synthesis of Semliki Forest virus (SFV) has been localized to large vesicle-like structures in SFV-infected cells and in COS cells transfected with a cDNA coding for the phosphoprotein (Peranen, J., *J. Gen. Virol* 72:195–199, 1991).

Nucleoside analogs that inhibit hepatitis B virus (HBV) replication also impair mitochondrial function after chronic exposure to the drugs, suggesting similar DNA replication mechanisms for both HBV and mtDNA. The analogs 2',3'-dideoxy-3'-thiacytidine, 5-fluoro-2', 3'-dideoxy-3'-thiacytidine and 1-(2'-deoxy-2'-fluoro-β-D-arabinofuranosyl)-5-iodouracil (i.e., fialuridine) inhibit HBV replication (Doong et al., *Proc. Natl. Acad. Sci. USA* 88: 8495–8499, 1991; Colacino et al., *Antimicrobid Agents and Chemother*. 38(9): 1997–2002, 1994). Of these, the (+)-enantiomer of 2',3'-dideoxy-3'-thiacytidine has been shown to significantly inhibit mtDNA synthesis in vitro in isolated mitochondria (Chang et al., *J. Biol. Chem.* 267(31): 22414–22420, 1992).

HBV is readily found in organs that contain large quantities of mitochondria, including the liver, pancreas and salivary gland, but in HBV-transfected cell lines that contain few mitochondria, HBV virus particles and antigens are difficult to detect. Moreover, some HBV antigens may be required for viral replication because cell lines that do not make HBV a proteins (HBe) also do not produce Dane particles. This may be because mitochondria are often damaged during conventional tissue or cell culture resulting in limited growth of HBV in the cultured cells. Hypoxia appears to be responsible for mitochondrial damage during conventional cell culture of mitochondria-rich cells. Some cell lines (e.g., modified adult hepatocytes, hepatoblastoma cells and fetal hepatocytes) have been found to producing HBe antigen in conventional tissue culture systems (Gripon et al., *Virol.* 192:534–540, 1993; Ochiya et al., *Proc. Natl. Acad. Sci. USA* 86:1875–1879, 1989). Such cell lines may contain enough mitochondria to allow HBe production using conventional tissue culture methods.

Recently, HBV transgenic mice have been constructed and used to examine the assembly, transport, secretion and other functional properties of HBV proteins (Guidotti et al., *J. Virol.* 69:6158–6169, 1995; Araki et al., *Proc. Natl. Acad. Sci. USA* 86:207.211, 1989). HBe antigen produced in such transgenic mice may result from the plasmids used to construct the transgenics or RNA produced from those plasmids entering the mitochondria. The possibility that the plasmids may enter the mitochondria is based on the fact that the mitochondrial membrane structure in similar to that of other membranes that allow passage of nucleic acids under certain conditions. High level HBV replication has been found in liver and kidney tissue of some HBV transgenic mice containing terminally redundant greater-than-genome length HBV constructs (Guidotti et al., *J. Virol.* 69:6158.6169, 1995).

Actively replicating HBV in humans, cell lines or transgenic animals that produce virus particles always also produce HBe (Chisari, F. V., *Hiepatology* 22:1316–1325, 1996). Both the universal and mitochondrial translation systems may be needed for replication of fully functional HBV. In hepatocytes, it appears that more HBV antigens are produced using the mitochondrial translation system than the universal translation system because most soluble HBV antigens are found in the mitochondrial fraction of cultured liver tissue (Paik et al., Abstract, Am. Assoc. for the Study of Liver Diseases, 1995). However, because mitochondria are often damaged in conventional tissue culture systems, the contribution of the mitochondrial translation system to viral assembly and/or immune reactions in vivo has been difficult to determine. This mitochondrial damage associated with conventional tissue culture methods may also explain why it has been difficult to propagate HBV in vitro using cell cultures.

Dynamic organ culture systems have been disclosed in which liver tissue viability can be maintained for about 24–48 hours under controlled conditions (Smith, P. F. et al., *Life Sci.* 36: 1367, 1985; S. S. Park, *Inje Med J.* 14(3): 363.369, 1993). The use of in vitro thymic organ culture has been described in connection with methods for identifying potential anti-viral agents (published PCT application WO 9505453).

The present invention uses a physiologic culture system (available from Leema Pharmed, Seoul, Korea) to culture animal tissue in vitro where it is effectively infected with a virus, including a human HBV or HCV, for production of viral antigens using a eucaryotic mitochondrial translation system. The system also can be used for producing other non mitochondrial proteins that can be translated in mitochondria by transfecting the cultured cells with a human hepatitis virus-based vector containing recombinant DNA. The preferred vector contains DNA from HBV and/or complementary to HCV sequences.

SUMMARY OF THE INVENTION

According to the invention, there is provided a method of producing viral antigens in cultured animal tissue comprising the steps of: providing organ tissue from an animal to serve as a host tissue in in vitro culture, wherein the host tissue is rich in mitochondria; infecting the host tissue in vitro with a virus; culturing the infected host tissue in vitro to produce viral proteins using a mitochondrial translation system in the host tissue; and isolating viral proteins from the infected and cultured host tissue. In one embodiment of the method, the host tissue is isolated from organ tissue selected from the group consisting of liver, kidney, pancreas and salivary gland. In another embodiment, the animal is selected from the group consisting of humans, rats, mice, dogs, chickens, and frogs. In a preferred embodiment, the virus is a human virus selected from the group consisting of hepatitis A virus, hepatitis B virus, hepatitis C virus and encephalitis virus. In one embodiment, the viral antigens are produced in mitochondria in the host tissue. In a preferred embodiment, the method further comprises introducing the isolated viral antigens into an animal to induce an immune response. In another preferred embodiment, viral antigens suitable for use in a vaccine are produced according to the method.

According to another aspect of the invention, there is provided a method of producing proteins in cultured animal tissue comprising the steps of: providing organ tissue from an animal to serve as a host tissue in in vitro culture, wherein the host tissue is rich in mitochondria; transfecting the host tissue in vitro with a DNA vector comprising a virus DNA and a recombinant DNA; culturing the transfected host tissue in vitro to produce proteins encoded by the transfected DNA vector using a mitochondrial translation system in the host tissue; and isolating proteins encoded by the transfected DNA vector from the cultured and transfected host tissue. In one embodiment of this method, the host tissue is isolated from organ tissue selected from the group consisting of liver, kidney, pancreas and salivary gland. In another embodiment, the animal is selected from the group consisting of humans, rats, mice, dogs, chickens, and frogs. In a preferred embodiment, the virus DNA is human hepatitis B virus DNA. The method may further comprise the step of infecting or transfecting the host tissue with a helper virus. In one embodiment, the proteins are produced in mitochondria in the host tissue. Another embodiment is proteins suitable for use in a vaccine produced according to the method. Preferred embodiments include proteins produced according to the method wherein the virus DNA is human hepatitis B virus DNA and wherein the DNA vector contains a recombinant DNA inserted into a human virus DNA sequence coding for a nonstructural viral protein.

DETAILED DESCRIPTION OF THE INVENTION

The present invention is for methods of producing natural proteins that cannot be produced readily using conventional recombinant DNA technology and proteins from viruses where the viral nucleic acid is translated in vitro in cells containing a large quantity of mitochondria where the cells are maintained in an automated dynamic culture system.

The present invention allows for cross-species viral infection of tissue that is maintained in vitro to allow protein production from the infecting virus. This is especially important for translation of human viruses in animal cells but is also useful for any cross-species infection of cells using human or non-human viruses and human or non-human tissue as the host tissue. For example, slices of rat liver can be infected with human HBV and the liver tissue can be maintained in an automated dynamic culture system that allows expression of viral antigens in vitro.

Organ tissue was isolated from an animal such as a rat using standard surgical procedures. Typically, the organ was one known to be rich in mitochondria such as liver, kidney, pancreas or salivary gland. The tissue was cut into slices of about 2 cm$^2$ pieces of about 260 $\mu$m thickness and infected with a virus such as HBV by incubating the tissue slices with the virus in culture medium. HBV was obtained from biopsy liver tissue obtained from an infected human patient. It will be understood by those skilled in the art that other viruses such as hepatitis A virus, hepatitis C virus, encephalitis virus and similar animal viruses could be substituted for HBV. As a control, slices of the same type of animal tissue were cultured in medium that had not been exposed to the virus.

Figure 1:
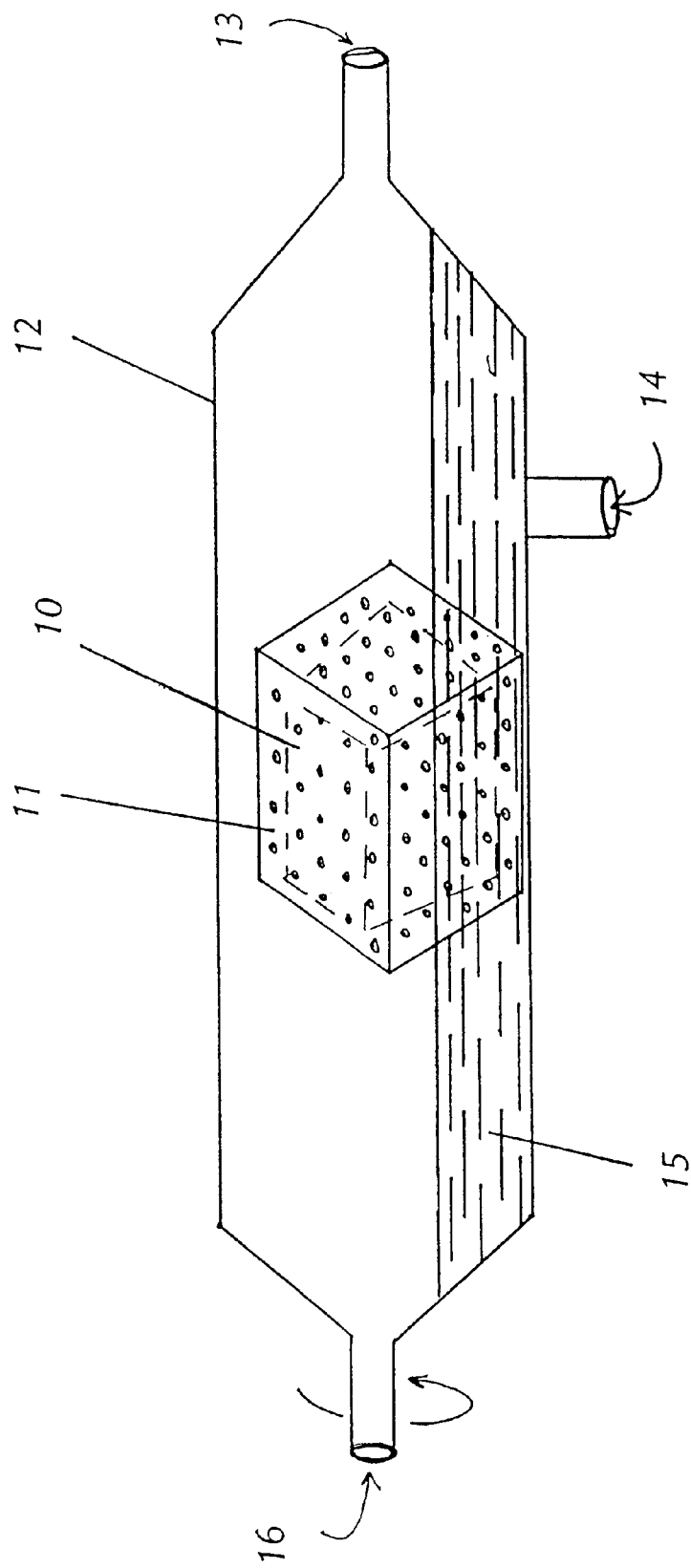
FIG. 1 shows a device for automated culturing of tissue samples in vitro.

The infected organ slices were cultured in an automated organ culture system. Referring to FIG. 1, in this culture system, the tissue slices 10 were cultured in a porous container 11 placed inside of a culture tube 12 which is rotatable (see arrow) to permit the tissue to be periodically immersed in the tissue culture medium 15 when the culture tube 12 is rotated. Gas exchange within the culture tube 12 occurred at regular intervals in which a gas mixture was introduced into the culture tube via ports 13, 16 located at the ends of the culture tube 12. Removal of samples for assaying or introduction of medium or other reagents was accomplished by accessing the inside of the culture tube 12 via a sample port 14 located in a wall of the culture tube 12.

The culture system was maintained at a constant temperature of 37° C. by placing it in an incubator.

The tissue slice was cultured at 37° C. in Modified Waymouth's MB 752/1 culture medium at pH 7.0, under 1.6 to 2 atm of a gas mixture of 5% $CO_2$ and 95% $O_2$ although those skilled in the art will appreciate that other media and gas mixtures can be equivalently used. Incubation of the virus-infected tissue was generally from about 1 to 48 hours, preferably about 24 hours.

After completion of the culture period, the tissue was collected and used to assay for or prepare proteins using standard techniques well known in the art. For example, standard immunochemistry methods were used to monitor for HBV proteins in the infected tissue by sectioning the tissue and staining it with anti-HBsAg antibody.

Generally, after less than 24 hours of culture, viral proteins were detected in the animal cells. The infected tissues were stained unevenly with the anti-HBsAg antibody, with the mitochondria-rich areas in the tissue being more intensely stained compared other portions of the tissue. The control tissue showed only background staining.

When the sectioned virus-infected animal tissue was examined using electron microscopy, multilayer membranous mitochondria-like organelles containing viral proteins were detected indicating that the efficiency of viral infection was related to the concentration of mitochondria in the animal tissue. Thus, cross-species viral infection of a human virus into animal tissue was demonstrated using HBV because the intense immunostaining of tissue with anti-HBsAg antibodies shows that HBV can infect and replicate in an animal organ that has sufficient mitochondria to allow viral replication.

Infected rat liver tissue that was examined by electron microscopy 6 to 24 hrs post-infection with HBV contained organeles with a double membrane that contained a large quantity of hepatitis B surface antigen (HBsAg) identified using immunochemistry specifically recognizing HBsAg and core antigen. Some of the immunostaining structures resembled broken cristae sections of mitochondria. Because mitochondria are known to have a translation system separate from that of the cytoplasmic translation system, the presence of HBsAg in mitochondria-like organelles suggested that the protein was translated by the mitochondrial translation system. Such translation would produce different secretory antigens from HBV compared to translation of the same RNA using the universal codon usage system in cellular cytoplasm.

HBV proteins isolated from the infected rat tissue show a profile of viral proteins using standard polyacrylamide gel electrophoresis that is more complex than HBV proteins produced by standard recombinant DNA technology. The immunostaining results suggest that the HBV proteins produced by the present method are translated using the mitochondrial translation system rather than the standard cellular ribosomal translation system. Thus, the proteins produced using the present method are more like viral proteins produced during a normal infection and therefore have antigenic properties as occur during infection. Such proteins produced using the present method can be used to produce an immune response in a mammal and the antigenic determinants may more closely resemble those produced during infection than determinants on proteins produced using standard recombinant DNA technology that relies on cellular ribosomal translation.

The invention also encompasses a method of producing proteins from cloned DNA contained within a viral-based vector where translation occurs in vitro in mitochondria-rich animal cells transfected with the vector where the cells are maintained in an automated dynamic culture system. An effective HBV-based expression system is used to produce proteins dependent on translation in mitochondria-rich tissue. In this embodiment of the invention, an HBV-based expression vector containing a cloned coding DNA sequence inserted in a structural HBV gene is used to direct gene expression of the cloned DNA in transfected animal organ tissue cultured in vitro using the preferred automated culture system.

Double-stranded HBV DNA (containing "minus" strand and "plus" strand DNA sequences) is used to construct a circular DNA vector into which other coding DNA sequences can be inserted using standard molecular biology methods. The HBV-based vector also contains sequences from the prokaryotic plasmid that allows the vector to be replicated in prokaryotes for amplification of the DNA. The vector contains a drug-resistance gene to provide a selectable marker in transfected cells (e.g., resistance to hygromycin B). The inserted coding DNA sequence is inserted into a HBV structural gene not required for replication in transfected animal cells. The inserted coding DNA sequence may be another viral gene sequence, a eucaryotic gene, a cDNA, a DNA amplified by a polymerase chain reaction, or a synthetic DNA sequence and insertion is accomplished using standard molecular biology methods of cutting and ligation to place the inserted DNA in proper frame and orientation to allow expression from the HBV sequences.

Because HBV replication has been found in liver and kidney tissue of some transgenic mice containing terminally redundant greater-than-genome length HBV constructs (Guidotti et al., *J. Virol.* 69:6158–6169, 1995), these results suggest that the transgenic constructs may have been transfected to the mitochondria rather than the nucleus. Thus, recombinant constructs containing greater-than-genome length HBV may also be useful for transfection into tissue maintained in vitro using the present system and are considered functionally equivalent to the constructs discussed herein for the present method.

The invention can be better understood by way of the following examples which are representative of the preferred embodiments.

EXAMPLE 1

HBV Infection in Vitro of Rat Kidney Tissue

A mixed breed white rat was anesthetized generally with ether and surgically opened in the belly region using methods well known in the art. Then, 10 ml of chilled (about 4° C.) Wisconsin solution (Viaspan, DuPont) was injected into the aorta after cutting the caval vein to allow perfusion. The kidneys were removed from the bloodless field and stored in chilled Wisconsin solution (about 4° C.). Slices of kidney tissue (e.g., 2 $cm^2$ pieces of about 260 $\mu$m thickness) were prepared and stored in chilled culture media. The slices were incubated with HBV obtained from biopsy liver tissue obtained from an infected human patient. The HBV inoculum was prepared by placing human liver biopsy tissue from patients having hepatitis B surface antigenemia in modified Waymouth's MB 752/1 medium for 3 hours at 37° C.; the biopsy samples were removed after 3 hours and the slices of rat organ tissue are then cultured in the medium. Generally the ratio of biopsy tissue to medium was 5–20 g of tissue to 10 ml of medium. As a control, slices of rat kidney tissue were cultured in medium that had not been exposed to human liver biopsy tissue.

The infected kidney organ slices were cultured in the automated organ culture system as shown in FIG. 1 in which an excised slice of organ tissue 10 is placed inside of a porous container 11 that is placed inside of a culture tube 12 which is rotatable and has at least one inlet port 13 for entry of gases, medium, growth factors and the like. The porous container 11 is made of any inert substance including but not limited to plastic mesh, nylon mesh or a semi-permeable membrane, but preferably is stainless steel mesh in the shape of a square or rectangular box and having an average pore size of about 100 to 500 $\mu$m. The culture tube 12 includes a resealable sampling port 14 for removal of samples of tissue culture medium 15. The sampling port 14 can also be used for injection of medium 15, viral particles, growth factors and other culture reagents or substances to treat the tissue sample in vitro. The organ tissue 10 is periodically immersed in the tissue culture medium 15 when the culture tube 12 is rotated. The box shape of the porous container 11 promotes turning of the sample when the culture tube is rotated 12 rather than the container staying in one position with the culture tube rotating around it. Gas exchange within the culture tube 12 occurs at intervals in which a gas mixture is introduced into the inlet port 13 and gas is expelled via an outlet port 16 of the culture tube 12. The culture tube 12 is maintained at a constant temperature of 37° C. (e.g., in an incubator which is not shown). The organ culture process is preferably automated to maintain the cells under the same conditions during the entire incubation period.

The tissue slice is cultured at 37° C. in Modified Waymouth's MB 752/1 culture medium at pH 7.0, under 1.6 to 2 atm of a gas mixture of 5% $CO_2$ and 95% $O_2$. The culture medium was prepared from Waymouth MB 752/1 powdered medium (Gibco), 10% fetal bovine serum, 2.2% sodium bicarbonate, 25 mM D-glucose, 1 $\mu$g/ml crystalline bovine zinc insulin, an antibiotics mixture containing 50 U/ml penicillin and 50 $\mu$g/ml streptomycin (Gibco) and distilled water. Gas exchange was made at intervals of 2.5 minutes and tissues were immersed into culture medium 4.5 times per minute by rotating the culture tube shown in FIG. 1.

Incubation of the HBV-infected kidney tissue was generally from about 1 to 48 hours, preferably about 24 hours. The tissue was then treated using standard immunochemistry methods by sectioning the tissue and staining it with anti-HBsAg antibody (purchased from SIGMA, St. Louis, Mo.) to determine the presence of HBV in the infected tissue.

Generally, after less than 24 hours of culture, HBsAg was detected in the kidney cells. The infected renal tissues were stained unevenly with the anti-HBsAg antibody, with the mitochondria-rich proximal tubules showing greater intensity of staining when compared to the relatively mitochondria-poor distal tubules. When the sectioned HBV-infected rat renal tissue was examined using electron microscopy, a significantly higher concentration of multi-layer membranous mitochondria-like organeles containing HBsAg was detected in the proximal tubules than in the distal tubules. Thus, the efficiency of HBV infection is related to the concentration of mitochondria in the animal tissue. These results also show that, contrary to current concepts of cross-species viral infection, HBV can infect and replicate in an animal organ that has sufficient mitochendria to allow replication of the HBV.

In addition to rat kidney tissue, liver tissue from dogs, mice, chickens and frogs have been successfully cultured using the automated culture system described above. It will be understood by those skilled in the art that such animal tissue may also be infected with HBV or other human or non-human viruses (e.g., hepatitis A and C or encephalitis viruses) that infect mitochondria-rich tissue to permit viral replication in this in vitro system. It will be understood by those skilled in the art that such animal tissue may also include human tissue infected with a human virus or an animal virus.

EXAMPLE 2

HBV Infection of Rat Liver Tissue is Localized to Mitochondrial Organelles

Liver tissue was surgically removed from a mixed breed white rat essentially as described for removal of kidneys in Example 1. The liver tissue was sliced and infected with HBV essentially as described in Example 1. The infected rat liver tissue was then incubated in the automated culture system for about 24 hours and the tissue was examined for presence of HBsAg and the HBV e antigen (HBeAg) using an enzyme linked immunosorbent assay that recognizes these antigens using techniques well known in the art (i.e., an HBV ELISA kit available from Abbott Laboratories). The infected tissue was also assayed for HBV DNA by DNA hybridization using standard Southern blotting techniques (essentially as described in Guidotti et al., *J. Virol.* 69:6158.6169, 1995).

The infected rat liver tissue was first fractionated into a cytoplasmic soluble (cytosol) fraction and a pellet containing mitochondria using a standard cell fractionation method (essentially as described by Jensen et al., *Biochim. et Biophys. Acta* 1180: 65–72, 1992). Briefly, the infected tissue slices were homogenized in a buffer (0.25 M sucrose, 0.1 mM EDTA and 1 mM Tris-HCl, pH 7.4) and centrifuged at low speed (700×g) to remove nuclei and any unbroken cells (the nuclear fraction). The supernatant was centrifuged at high speed (12,000×g) to separate the mitochondrial fraction (in the pellet) and the cytosol fraction (in the supernatant). The nuclear, mitochondrial and cytosol fractions were then tested for the presence of HBsAg and HBeAg using the ELISA method to detect these two antigens.

The mitochondrial fraction contained at least 10-fold more HBsAg than was found in either the nuclear or cytosol fractions. The HBeAg was detected only in the mitochondrial fraction and was not found in the nuclear or cytosol fractions. These results indicate that HBV replicates in rat liver tissue primarily in mitochondria or mitochondria-like organelles that fractionated together with only limited HBV replication occurring in cellular nuclei.

Using standard gel separation and DNA hybridization techniques, replicating complexes consisting of HBV DNA of less than or equal to 2.1 Kb were found in the mitochondrial fractions. No HBV DNA was detected in the cytosol fraction and a minor amount (less than about 10% of that found in the mitochondrial fraction) was found in the nuclear fraction.

EXAMPLE 3

Comparison of HBsAg Isolated from Human Plasma with HBsAg Produced from Recombinant DNA HBsAg in a vaccine derived from human plasma (Hepavax obtained from Blue Cross, Korea) were compared to HBsAg made by recombinant DNA technology (obtained from JEIL-JEDANG, Seoul, Korea) using SDS-polyacrylamide gel electrophoresis (SDS-PAGE). The proteins were dissolved in a buffer containing 40 mM Tris-HCl, pH 6.8, 1% SDS, 0.35% β-mercaptoethanol, 5% glycerol and bromophenol blue and were boiled for 5 min before separation on a 10% SDS-PAGE gel using standard methods (Laemmli, U. K., Nature 227: 680–685, 1970). After electrophoresis, the proteins were immunoblotted using well known methods and anti-HBsAg antibody (obtained from SIGMA, St. Louis, Mo.).

The HBsAg produced by recombinant DNA technology showed only a single band at 23 Kd whereas the HBsAg isolated from human plasma showed a wide spectrum of surface antigens in a broad smeared band from about 20 Kd to about 30 kD. These results suggest that many naturally occurring HBV antigens may be produced in mitochondria using core antigen genes and the codon usage unique to mitochondria compared to the single protein produced by recombinant DNA technology. Because plasma-derived vaccine is generally more effective than vaccine produced by recombinant DNA technology, these results also suggest that multiple different forms of HBV surface antigens produced during infection may individually or together serve as better immunogens than a single HBV antigen produced by recombinant DNA technology.

EXAMPLE 4

Production of HBsAg in Mitochondria Using Mitochondrial Translation System

In the codon usage system of mammalian mitochondria, the codons AGA and AGG serve as stop codons to terminate translation. The gene for the core HBsAg contains AGA and AGG codons which have been presumed to be cleavage sites for processing of core antigen protein into mature HBsAg. However, when translated in mammalian mitochondria, the gene for core HBsAg is naturally terminated at the AGA and AGG codons. Based on the mitochondrial genetic codon usage, there are several other predicted initiation and termination codons in the HBsAg gene (summarized in Table 1). The same determinations have been made for the genes coding for the HBV proteins called pre-S1 and pre-S2 and core antigen (HBcAg) and these initiation and termination codon loci are also shown in Table 1 (for a general discussion of HBV proteins see Lau and Wright, *Lancet* 342: 1335–1340, 1993).

Rat liver tissue is infected with HBV essentially as described in Example 2 and the infected rat tissue is cultured in vitro for 12–48 hours. After incubation, the infected rat tissue is collected and lysed in a buffer containing 40 mM Tris-HCl, pH 6.8, 1% SDS, 0.35% β-mercaptoethanol, 5% glycerol and bromophenol blue. The lysate is boiled for 5 min and separated on a 10% SDS-polyacrylamide gel by electrophoresis (SDS-PAGE) using standard methods (Laemmli, U. K., *Nature* 227: 680–685, 1970). For comparison, HBsAg prepared by recombinant DNA technology is included as a control in an adjacent lane of the SDS-PAGE gel. Following separation by electrophoresis, the proteins are immunoblotted and detected with anti-HBsAg antibody using well known techniques.

HBsAg produced in the infected rat tissue grown in vitro contains proteins of about 20 Kd to about 30 Kd similar to those detected in plasma of humans infected chronically with HBV. Thus, translating HBV genes in vitro in mitochondria-rich tissue produces a variety of secretory antigens that mimic those that are naturally produced in infected humans. In contrast, the HBsAg produced by recombinant DNA technology appears as a single band of about 23 Kd. The multiple HBsAg proteins produced by in vitro infection of rat liver are isolated for use as a vaccine against HBV infection.

TABLE 1

| | Initiation Codon | | | | | |
|---|---|---|---|---|---|---|
| | #amino | | Termination Codon | | | |
| Protein Size | acids | AUA | AUG | AUU | AGA | AGG |
| HBsAg | 226 | 28<br>195 | 1<br>75<br>86<br>103<br>197<br>198 | 218<br>226 | 24<br>27 | none |
| pre-S1 | 119 | 85 | 1 | none | 104[1]<br>114 | 104[2] |
| pre-S2 | 55 | none | 1 | none | 16 | 18<br>48 |
| HBcAg | 183 | none | 1 | 59<br>105<br>126 | 98<br>112<br>133<br>150[3] | 56 |

[1]Found in the "adr" subtype of HBV.
[2]Found in the "adw" and "ayw" subtypes of HBV.
[3]This represents the end codon of HBeAg; previously presumed to be a cleavage site for a protease in plasma or cytoplasm.

EXAMPLE 5

Production of Proteins in Transfected Animal Tissue using an HBV-based Expression Vector An effective HBV-based expression system may similarly be used to produce proteins dependent on translation in mitochondria-rich tissue. That is, an HBV-based expression vector may be used to direct gene expression of a cloned DNA in transfected rat organ tissue cultured in vitro as disclosed in Examples 1 and 2.

HBV is a DNA virus having a 3200 base genome comprised of a "minus" strand and a shorter "plus" strand that together make a partly double-stranded circular DNA that encodes structural proteins and proteins required for viral replication (Lau and Wright, *Lancet* 342: 1335–1340, 1993).

A HBV-based vector contains sequences from the prokaryotic plasmid pBR322, HBV origin of replication, a truncated HBV polymerase gene and a drug-resistance gene (e.g., a hygromycin B phosphotransferase gene under the control of HSV thymidine kinase regulatory sequences, providing resistance to hygromycin B).

Referring to FIG. 2, the HBV-based vector, called pHBVex, comprises DNA sequences from the prokaryotic vector pBR322 (labeled "pBR") to allow replication of the vector in prokaryotic cells including *Escherichia coli*, sequences (labeled "AmpR") that confer ampicillin resistance when expressed in *E coli*; a hygromycin B phosphotransferase gene (labeled "HYG") under the control of HSV thymidine kinase promoter (labeled "HSV TK pro") sequences and termination sequences (labeled "HSV TK") that make eucaryotic cells expressing the gene resistant to hygromycin B; an insertion DNA sequence (labeled "insDNA") which can be genomic or cDNA sequences coding for the protein to be expressed under the control of a truncated HBV polymerase gene (labeled "HBVp"). The truncation of the HBV polymerase gene and insertion of foreign DNA occurs in the region between the terminal protein for replication and packaging and the beginning of the pre-S1 gene. The remainder of the plasmid is made of HBV "minus" strand DNA (labeled "HBV") and its standard complementary DNA sequence made by standard molecular genetic techniques including reverse transcription, DNA polymerization from a synthetic primer and ligation of the double stranded DNA representing the HBV "minus" strand into the remaining portions of the vector (Sambrook et al., *Molecular Cloning, A Laboratory Manual* (2nd Ed.), Vol. 1–3, Cold Spring Harbor Laboratory, Cold Spring Harbor, N.Y., 1989).

In the pHBVex vector, part of the coding sequence of the HBV polymerase gene is replaced with a foreign DNA sequence (either a viral or eucaryotic gene, cDNA or DNA amplified by a polymerase chain reaction) using standard molecular biology methods (Sambrook et al., *Molecular Cloning. A Laboratory Manual*, 2nd Ed., Vol. 13, Cold Spring Harbor Laboratory, Cold Spring Harbor, N.Y., 1989) of restriction enzyme digestion and ligation to place the insertion DNA in proper frame and orientation to allow expression from the HBV regulatory sequences. The arrows inside the circle indicate the orientation (direction of transcription) of the DNA sequences.

Figure 2:
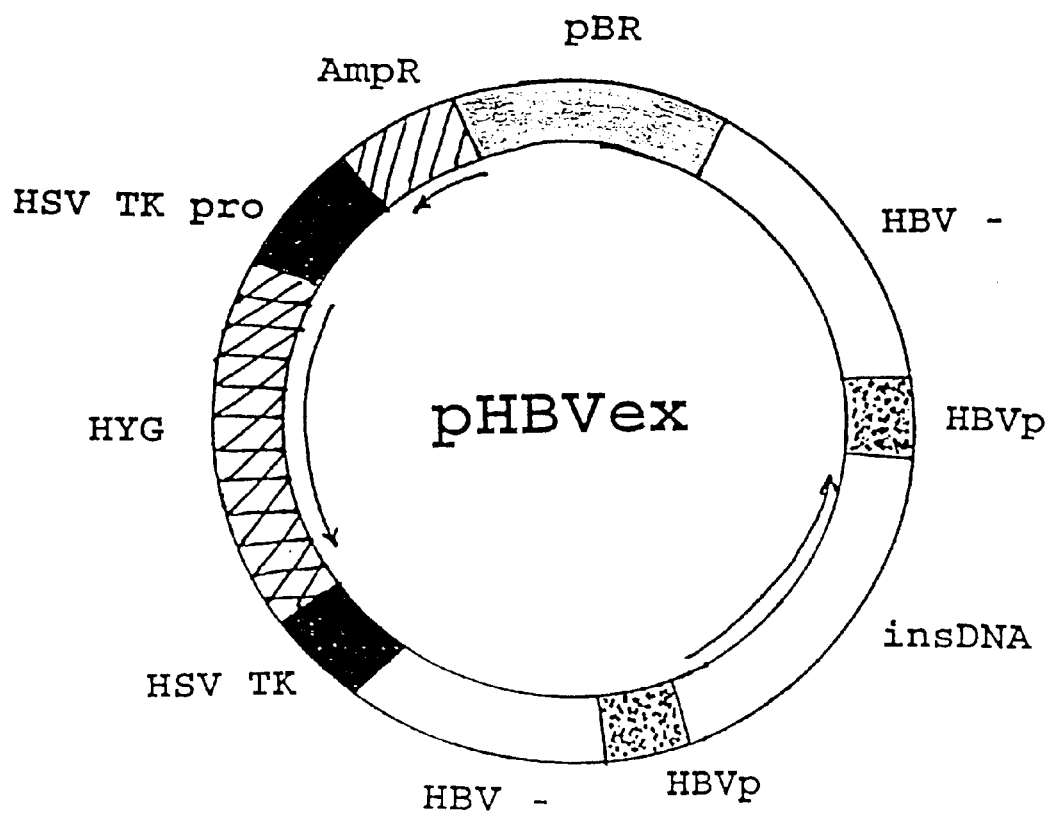
FIG. 2 diagrammatically shows a HBV-based expression vector.

Other DNA sequences in an equivalent pHBVex vector (not shown) may include sequences derived from other prokaryotic vectors, from hepatitis A virus, hepatitis C virus or other viruses including Epstein Barr virus (EBV), herpes simplex viruses (HSV) and encephalitis viruses. It will be understood by those skilled in the art that other HBV-based expression vectors could be substituted as equivalents for the vector diagrammed in FIG. 2. For example, a vector similar to pHBVex but containing a redundant greater-than-single HBV genome construct in the vector may be optimal for replication or gene expression analogous to the results obtained in transgenic mice containing redundant HBV constructs (Guidotti et al., *J. Virol* 69:6158–6169, 1995). It will further be appreciated by those skilled in the art that transfection using the pHBVex vector or an equivalent vector could also include co-transfection or infection with a helper virus to promote or enhance replication or gene expression of the vector DNA.

Animal tissue is isolated from mitochondrial-rich organs and prepared for in vitro culture essentially as described in Examples 1 and 2. The pHBVex vector containing insertion DNA is transfected into the mitochondria-rich tissue using standard transfection methodology including calcium phosphate precipitation, fusion of tissue cells with bacterial protoplasts containing a pHBVex-insDNA construct, treatment of the tissue with liposomes containing the pHBVex-insDNA sequence, DEAE dextran promoted transfection, electroporation and microinjection of the DNA.

The transfected tissue slices are cultured in vitro in the automated system essentially as described in Example 1 to allow protein production resulting from expression of the transfected DNA in the mitochondrial-rich tissue. The protein is purified using any of a variety of standard methods including affinity chromatography. Using the HBV-based expression system, other viral antigens that mimic those produced during natural infection of viruses that infect mitochondria-rich tissue (e.g., other hepatitis viruses or encephalitis viruses) may be produced to make effective vaccines for these pathogens.

EXAMPLE 6

Production of Human HCV Antigens in Transfected Animal Tissue using HBV-based Expression Vector Because directly culturing HCV in animal tissue in a dynamic tissue culture system may still be an inefficient method to obtain sufficient HCV antigens (e.g., because HCV replicates relatively slowly), using a vector based on another virus is a valid option for producing HCV antigens in vitro. The pHBVex vector is used to transfer genes coding for antigens of human hepatitis C virus into mitochondria-rich cells for production of natural antigens using the mitochondrial translation system essentially as described in Example 5. Because hepatitis C virus is an RNA virus, the RNA sequence coding for hepatitis C surface antigen (HCsAg) is first reverse transcribed into a cDNA using techniques well known in the art (Sambrook et al., *Molecular Cloning, A Laboratory Manual* (2nd Ed.), Vol. 1–3, Cold Spring Harbor Laboratory, Cold Spring Harbor, N.Y., 1989. The HCsAg cDNA is inserted into the truncated HBV polymerase gene of the pHBVex vector using standard techniques of restriction digestion of the vector DNA and ligation (using appropriate restriction enzyme cut sites or blunt end ligation) of a double stranded cDNA coding for the HCsAg. The pHBVex-HCsAg construct is transfected into isolated slices of rat liver tissue and cultured in vitro for 24–48 hr using essentially the methods described in Examples 1, 2 and 5. After 24–48 hr of culture, the tissue is removed and HCsAg protein produced in the transfected tissue is purified using standard protein purification techniques including affinity chromatography using antibody that binds to HCsAg protein.

The present invention includes a useful method for making proteins that are naturally produced in mitochondria-rich cells (e.g., proteins produced in liver or pancreas). The translation method of the present invention can be used for producing natural non-nitochondrial proteins that are translated in mitochondria. This can be especially important in producing proteins that have immunogenic characteristics such as processing or codon recognition dependent on mitochondrial translation. That is, the present invention is useful for producing natural antigens of viruses that replicate in mitochondria, or those which replicate too slowly when cultured using conventional tissue culture methods, or those that cannot be produced using conventional recombinant DNA technology. There is a need to produce proteins from infectious agents, particularly human infectious agents, in an in vtro system. A cross-species infection is preferable because it limits the danger of contamination of the desired product with an undesired product from the same species. For example, a method of infection with a human infectious agent that does not rely on human cells for growth of the infectious agent limits the danger of contamination from other human infectious agent (e.g., HIV present in human tissue). Similarly, there is a need for an in vitro system which effectively mimics human infection to produce immunogens that resemble those produced during human infection which may not be possible using conventional techniques used to produce protein from recombinant DNA. The invention provides a method of protein production using a recombinant HBV-based vector which is useful for directing production of other non-mitochondrial proteins in mitochondria of transfected animal cells. The invention also allows one to grow virus in an in vitro system that is useful for discovery of new therapeutics to prevent disease and improve the current treatments of pathological conditions caused by virus infection in humans.

What is claimed is:

1. A method of isolating a viral antigen from cultured animal tissue comprising the steps of:

providing organ tissue from an animal to serve as a host tissue in in vitro culture, wherein said host tissue is rich in mitochondria;

infecting said host tissue in vitro with a virus so as to establish an infected host tissue;

culturing said infected host tissue in vitro to produce a viral antigen using a mitochondrial translation system in said host tissue;

recovering a mitochondrial fraction from said infected host tissue; and isolating a viral antigen from said mitochondrial fraction.

2. The method of claim 1, wherein said host tissue is isolated from organ tissue selected from the group consisting of liver, kidney, pancreas and salivary gland.

3. The method of claim 1, wherein said animal is selected from the group consisting of humans, rats, mice, dogs, chickens, and frogs.

4. The method of claim 1, wherein said virus is a human virus selected from the group consisting of hepatitis A virus, hepatitis B virus, hepatitis C virus and encephalitis virus.

5. The method of claim 1, wherein said viral antigen is produced in mitochondria in said host tissue.

6. A method of isolating a protein from cultured animal tissue comprising the steps of:

providing organ tissue from an animal to serve as a host tissue in in vitro culture, wherein said host tissue is rich in mitochondria;

transfecting said host tissue in vitro with a DNA vector comprising a virus DNA and a recombinant DNA so as to establish a transfected host tissue;

culturing said transfected host tissue in vitro to produce a protein encoded by said DNA vector using a mitochondrial translation system in said transfected host tissue;

recovering a mitochondrial fraction from said transfected host tissue; and isolating a protein encoded by said DNA vector from said mitochondrial fraction.

7. The method of claim 6, wherein said host tissue is isolated from organ tissue selected from the group consisting of liver, kidney, pancreas and salivary gland.

8. The method of claim 6, wherein said animal is selected from the group consisting of humans, rats, mice, dogs, chickens, and frogs.

9. The method of claim 6, wherein said virus DNA is human hepatitis B virus DNA.

10. The method of claim 6, further comprising the step of infecting or transfecting said host tissue with a helper virus.

11. The method of claim 6, wherein said protein is produced in mitochondria in said host tissue.

* * * * *